United States Patent [19]

Byrne et al.

[11] Patent Number: 4,826,490

[45] Date of Patent: May 2, 1989

[54] SAFETY DEVICE FOR HYPODERMIC NEEDLE OR THE LIKE

[75] Inventors: Phillip O. Byrne; Penelope R. Sisson; Harry R. Ingham, all of Newcastle upon Tyne, England

[73] Assignee: National Research Development Corporation, London, England

[21] Appl. No.: 888,376

[22] Filed: Jul. 23, 1986

[30] Foreign Application Priority Data

Jul. 29, 1985 [GB] United Kingdom ............... 8519049

[51] Int. Cl.⁴ .............................................. A61M 5/00
[52] U.S. Cl. .................... 604/198; 604/110; 206/365
[58] Field of Search ............... 604/110, 262, 192–198, 604/263; 206/364, 365

[56] References Cited

U.S. PATENT DOCUMENTS

| | | | |
|---|---|---|---|
| 2,876,770 | 10/1955 | White | 604/263 |
| 2,925,083 | 12/1957 | Craig | 604/197 |
| 3,323,523 | 6/1967 | Scislowicz et al. | 604/162 |
| 3,574,306 | 4/1971 | Alden | 604/162 |
| 3,610,240 | 10/1971 | Narautuneian | 604/162 |
| 3,658,061 | 4/1972 | Hall | 604/263 |
| 3,884,230 | 5/1975 | Wulff | 604/197 |
| 3,904,033 | 9/1975 | Haerr | 604/263 X |
| 4,170,993 | 10/1979 | Alvarez | 604/180 |
| 4,425,120 | 1/1984 | Sampson et al. | 604/198 |
| 4,573,976 | 3/1986 | Sampson et al. | 604/198 |
| 4,664,259 | 5/1987 | Landis | 206/365 |
| 4,666,435 | 5/1987 | Braginetz | 604/198 |

FOREIGN PATENT DOCUMENTS

| | | |
|---|---|---|
| 813433 | 7/1951 | Fed. Rep. of Germany . |
| 924734 | 5/1963 | United Kingdom . |
| 1233302 | 5/1971 | United Kingdom . |
| 1297746 | 11/1972 | United Kingdom . |
| 2059268 | 4/1981 | United Kingdom . |
| 2114006 | 8/1983 | United Kingdom . |

Primary Examiner—Dalton L. Truluck
Attorney, Agent, or Firm—Cushman, Darby & Cushman

[57] ABSTRACT

A safety device for a hypodermic needle or for a similar instrument used in the clinical puncture of the skin comprises a sheath (6, 25 or 32) adapted to be connected to the needle (5, 21 or 33) or to a support (4 or 31) for the needle. The sheath is so connected in a first position (FIG. 1A, 2A, or 3A) which permits normal use of the needle and can be placed, by movement relative to the needle (FIG. 1B or 3B) or by folding upon itself (FIGS. 2B and 2C) in a second position in which the needle is encapsulated by the sheath. The sheath is retained in that second position, for example by a projection (9, 27 or 35) extending into a slot (10 or 36) or through an aperture (28).

10 Claims, 3 Drawing Sheets

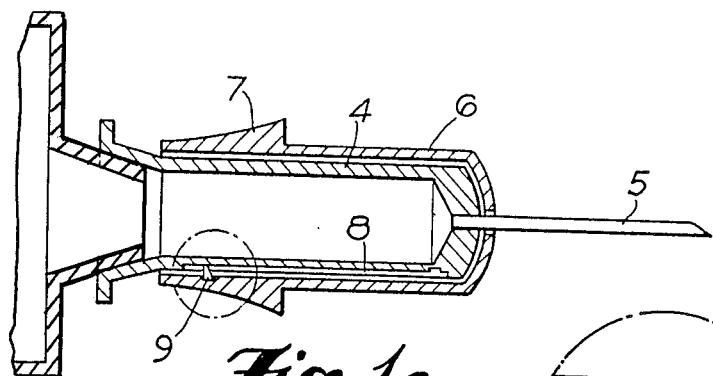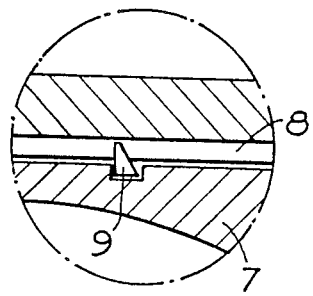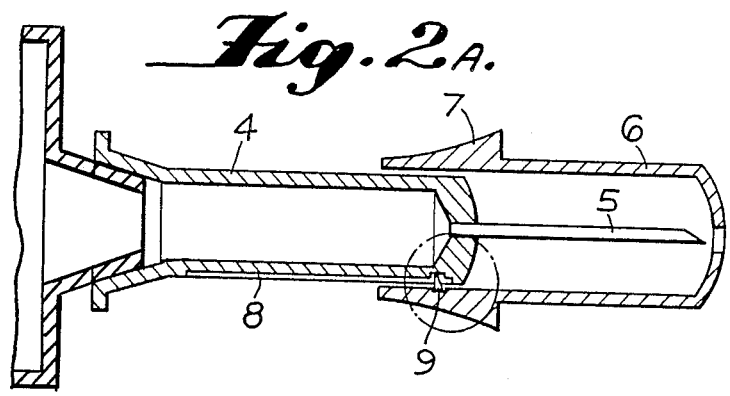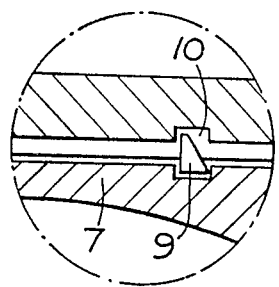
Fig. 1A.
Fig. 1B.
Fig. 2A.
Fig. 2B.

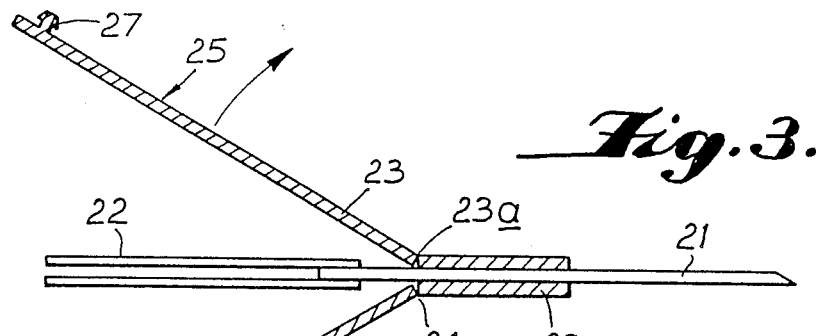
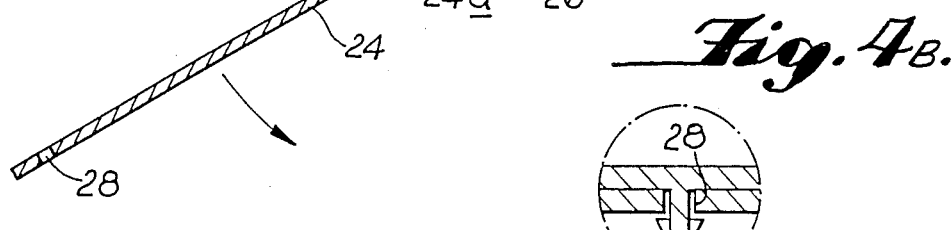
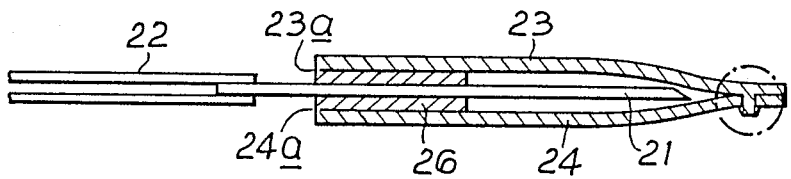
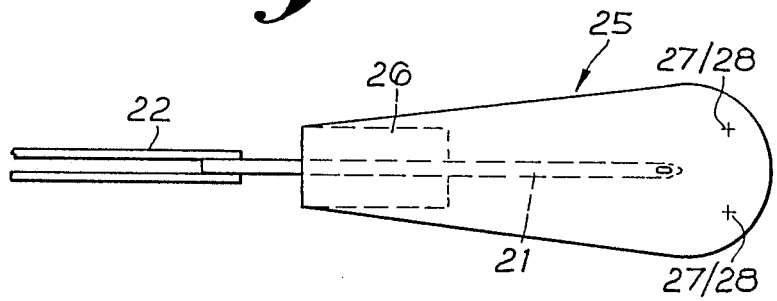

SAFETY DEVICE FOR HYPODERMIC NEEDLE OR THE LIKE

The present invention is a safety device for a hypodermic needle or similar instrument used in the clinical puncture of the skin.

The taking of blood samples from persons in hospitals, health centres or other clinical areas is a routine medical procedure, as is the injection of pharmaceutical preparations or biological materials. However, many incidents have been reported in the press and in medical journals of clinical operators subsequently accidentally wounding themselves or other persons with the needle and thereby either transmitting a disease or causing chemical or biological poisoning.

There is a clear need for a device which permits the disposal of a hypodermic needle or such instrument in a manner which protects the clinical operator, observers of the clinical procedure and all other persons concerned, including the general public, from accidental wounding.

It is an object of the present invention to provide such a device.

The safety device according to the invention for a hypodermic needle or similar instrument comprises a sheath, adapted to be connected to said needle or other instrument or to a support therefor in a first position which permits normal use of said needle or other instrument and to be placeable, by movement relative to the needle or other instrument or by folding upon itself, in a second position in which the needle or other instrument is encapsulated by the sheath and the sheath is retained in that second position.

As indicated, the safety device of the present invention is generally applicable to the protection of puncturing instruments typified by hypodermic needles, although among such instruments hypodermic needles are by far the most widely used. For example, the device may be applied to the protection of biopsy needles, winged needles, that is needles provided with lateral attachments to enable them to be affixed to the skin surface as by adhesive tape, and to intravenous cannulas and lumbar puncture needles. For convenience, the invention is hereinafter described specifically as applied to "needles", in particular hypodermic needles, but it is emphasised that the invention is not to be limited thereby.

The sheath is adapted to be attached to the needle or to a support for the needle but may be provided separately from the needle, to be attached to the needle or support at the point of use, either before or after the needle has actually been used. It is much preferred that such separate sheaths be attached before use, so that the needle may be more readily encapsulated immediately after it has been used. However, the sheath according to the present invention is preferably and conveniently supplied already attached to the needle. In particular, it is preferably attached either irremovably or in a way which makes its removal difficult. For example, the sheath may be adhered to the needle or to a support for the needle or may be clipped to the needle or support.

When the needle is designed for use without a syringe or remote from an associated syringe, to which it is then linked by a flexible tube, then the sheath is preferably secured direct to the needle. The sheath may then conveniently incorporate one or more parts which are foldable relative to the body of the sheath and thereby to encapsulate the needle.

When the needle, on the other hand, is mounted upon a housing designed to be attached to a syringe barrel or luer connector, then the sheath may advantageously be secured to the housing. The sheath may then be capable of movement relative to the housing in a direction which has a component parallel to the length of the needle, so that the sheath may be moved along the length of the needle until the latter is fully encapsulated. This relative movement of sheath and housing may for example be a linear sliding movement or a spiral movement, as more particularly exemplified hereinafter in FIGS. 3A and 3B of the drawings.

Such relative movement of sheath and housing may be determined by one or more liner or spiral grooves or channels in the housing engaging one or more lugs or other projections on the sheath—or grooves or channels in the sheath engaging projections on the housing.

In the second position of the sheath, in which the needle is encapsulated, the sheath is retained against further movement relative to the needle. That retaining of the sheath is preferably irreversible or reversible only with difficulty. For example, one or more lugs or other projections on one of the relatively movable components may engage one or more apertures or slots in the other component, preferably under the pressure of a natural resilience in at least one of the components or under pressure from one or more springs.

The sheath may advantageously and conveniently be made from a resilient plastics material, for example polypropylene, and the housings may be made from the same, or a similar, material.

The invention will now be further described with reference to the accompanying drawings, wherein:

FIG. 1A is a sectional view of a first embodiment of the safety device according to the present invention, in a position in which the needle may be used normally;

FIG. 1B is an enlarged detailed view of the circle portion of FIG. 1A;

FIG. 2A is a view corresponding to that of FIG. 1A but with the sheath moved to encapsulate the needle; and FIG. 2B is an enlarged detailed view of the circle portion of FIG. 2A.

FIG. 3 is a sectional view of a second embodiment of the safety device according to the present invention, in a position in which the needle may be used normally;

FIG. 4A is a view corresponding to that of FIG. 3 but with the sheath folded to encapsulate the needle;

FIG. 4B is an enlarged view of the circled portion of FIG. 4A;

FIG. 4C is a plan view of the device in the position shown in FIG. 4A;

Figure 5A:
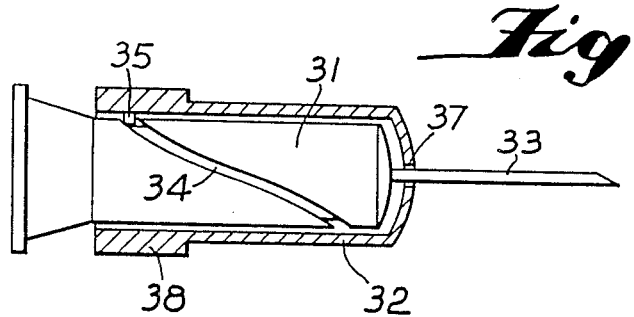
FIG. 5A is a view, partly in section, of a third embodiment of the safety device according to the present invention, in a position in which the needle may be used normally.

The embodiment of the invention shown in FIGS. 1A and 1B comprises a needle housing 4 in the form of a plastics moulding carrying a needle 5 and, slidably supported upon the housing 4, a plastics sheath 6 incorporating a thumbguard 7 integral therewith. Also incorporated in the housing 4 and running lengthwise, is a channel 8. The sheath 6 incorporates a self-springed spigot 9 which slides along the channel 8, as shown in more detail in the enlarged inset. When the sheath travels to the end of the channel 8, the self-springed spigot 9 drops into a small "well" 10, thus locking the sliding sheath in position. The length of the sheath is such that, when it is locked in position, the sharp end of the needle is completely enclosed by the sheath, as shown in FIG. 1B.

The housing 4 is designed to mate with any standard syringe barrel or luer connector. After use, the protective sheath is extended into the locked position, thus encapsulating the needle in a safe manner.

The embodiment of the invention shown in FIGS. 3–4C is designed to allow encapsulation of a hypodermic needle 21 which is tethered to a syringe by an extension tube 22. The needle 21 is sandwiched between two plastics mouldings or pressings 23,24 which together form a sheath 25. A part 26 of the sheath 25 is permanently attached to the hypodermic needle. At points 23a and 24a the plastic is formed in a manner which allows the free ends of members 23 and 24 to hinge as indicated. Near to its outer end, the member 23 carries two spigots 27, which are designed to mate with holes 28 in the member 24 (when the sheath is in its folded position) and lock the sheath securely around the needle 21.

Figure 5B:
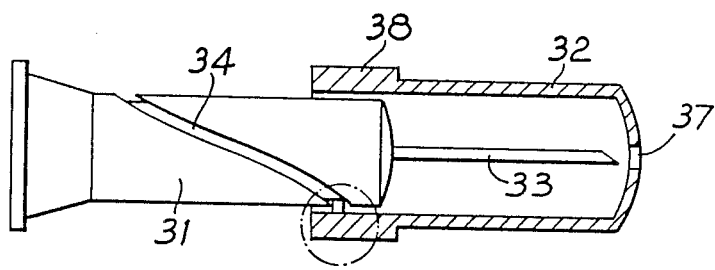
FIG. 5B is a view corresponding to that of FIG. 5A but with the sheath moved to encapsulate the needle.
Figure 5C:
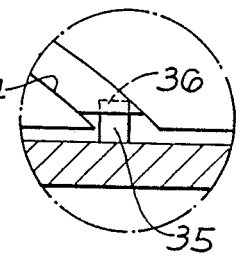
FIG. 5C is an enlarged view of the circled portion of FIG. 5B.

The third embodiment of the invention, as illustrated in FIGS. 5A–5C, comprises a needle housing 31 in the form of a plastics moulding, a plastics sheath 32 which is free to rotate thereon and a needle 33. Impressed into the housing 31 is a helical groove 34 extending from near the end of the housing 31 which is distal to the needle 33 towards the needle. The sheath 32 has a self-springed spigot 35 which fits into, and is free to move along, the helical groove 34. As shown in FIG. 5B, rotation of the sheath 32 in a clockwise direction (viewed from the rear) will result in a forward motion causing the sheath to encapsulate the needle 33. At the end of its travel the springed spigot 35 drops into a "well" 36 thereby locking the sheath in position. The length of the sheath 32 is such that when it has reached this locked position the needle is completely encapsulated and withdrawn beyond the orifice 37 in the outer end of the sheath.

The device shown in FIGS. 5A and 5B is designed to mate with any standard syringe barrel or luer connector. After use, the protective sheath is placed in position by applying a twisting force to the sheath. To facilitate the application of this twisting force, a raised section 38 may be incorporated into the sheath's surface.

This form of the invention may be fabricated with one or more helical grooves, which may extend in a clockwise or anti-clockwise direction. For greater mechanical strength and stability, a double helix may be preferred.

We claim:

1. For use with clinical apparatus operably applied to a patent by way of skin puncture, a disposable non-reusable hypodermic needle assembly comprising:
   a needle support housing having a connector formation for removable attachment with said apparatus;
   a hypodermic needle supported by said housing for communication with said apparatus by way of said formation, one end portion of said needle projecting from said housing remotely from said formation;
   a sheath surrounding said housing and mounted thereon for movement in the longitudinal direction of said needle from a first position nearer to said formation and in which first position said needle one end portion is exposed to effect said puncture, to a second position further from said formation and in which second position said needle one end portion is enclosed within said sheath;
   a strop mechanism effective to constrain said sheath against movement from said first position towards and around said apparatus; and
   locking means irreversibly automatically operable to secure said sheath in said second position upon said movement into such position, said locking means having two elements respectively located on the interior of said sheath and on a portion of said needle housing covered by said sheath in said second position so that said locking means is, when operated, wholly between said sheath and said housing.

2. An assembly according to claim 1 wherein, to serve as said stop mechanism, said housing has a portion with external dimensions transversely of said longitudinal direction which are enlarged relative to the remainder of the housings, and said sheath has lesser corresponding internal transverse dimensions surrounding said housing than said portion.

3. An assembly according to claim 2 wherein said housing connector formation includes said transversely enlarged portion.

4. An assembly according to claim 1 comprising guide means on said housing to guide said sheath between said first and second positions.

5. An assembly according to claim 4 wherein said guide means comprises a channel formed in one of said housing and sheath to extend in said longitudinal direction, and a projection from the other one of said housing and sheath, said channel and projection being mutually engaged.

6. An assembly according to claim 5 wherein said locking means comprises a well formed in one end of said channel to receive said projection in irreversible engagement therein.

7. An assembly according to claim 6 wherein, to serve as said stop mechanism, the other end of said channel is closed.

8. An assembly according to claim 1 wherein said locking means comprises a projection from one of said housing and sheath, and a well formed in the other of said housing and sheath to receive said projection in irreversible engagement therein.

9. Clinical apparatus for application to a patient by way of skin puncture, comprising:
   a chamber operable in one of two modes respectively to apply and draw fluent material to and from said patient;
   a non-reusable hypodermic needle assembly including a support housing attached with said chamber, and a hypodermic needle connected with said housing for communication with said chamber, said needle having one end portion projecting from said housing remotely from said chamber; and
   a sheath surrounding said assembly and mounted thereon for limited movement in the longitudinal direction of said needle from a first position to a second position, said first position being removed from but nearer to said chamber to expose said needle one end portion, and said second position being further from said chamber to cover said needle one end portion;

said assembly and sheath being provided with respective elements of a locking mechanism means irreversibly automatically cooperable to secure said sheath in said second position upon said movement into such position, said elements being respectively located on the interior of said sheath and on a portion of said needle assembly covered by said sheath in said second position so that said elements are, when operated, wholly between said sheath and said assembly.

10. Apparatus according to claim 9 wherein said locking means elements comprise a projection and a well to receive said projection in irreversible engagement therein.

* * * * *

UNITED STATES PATENT AND TRADEMARK OFFICE
CERTIFICATE OF CORRECTION

PATENT NO. : 4,826,490

DATED : May 2, 1989

INVENTOR(S) : BYRNE, Phillip O.; SISSON, Penelope R.; INGHAM, Harry R.

It is certified that error appears in the above-identified patent and that said Letters Patent is hereby corrected as shown below:

Column 4, line 7 -- "strop" should read stop.

Column 4, line 23 -- "housings" should read housing.

Signed and Sealed this
Twenty-sixth Day of December, 1989

Attest:

JEFFREY M. SAMUELS

Attesting Officer     Acting Commissioner of Patents and Trademarks

UNITED STATES PATENT AND TRADEMARK OFFICE
CERTIFICATE OF CORRECTION

PATENT NO. : 4,826,490
DATED : May 2, 1989
INVENTOR(S) : BYRNE, et al

It is certified that error appears in the above-identified patent and that said Letters Patent is hereby corrected as shown below:

Column 3, line 58, delete "patent" and insert --patient--.

Signed and Sealed this

Twentieth Day of August, 1991

Attest:

HARRY F. MANBECK, JR.

Attesting Officer

Commissioner of Patents and Trademarks